United States Patent [19]
Gougeon

[11] Patent Number: 6,019,604
[45] Date of Patent: Feb. 1, 2000

[54] RESILIENT DENTAL PROSTHESIS CONNECTING STRUCTURE

[76] Inventor: Sylvain Gougeon, 3590 Ridgewood #406, Montreal, Que, Canada, H35 1C2

[21] Appl. No.: 08/920,457

[22] PCT Filed: Dec. 4, 1996

[86] PCT No.: PCT/CA96/00811

§ 371 Date: Sep. 16, 1997

§ 102(e) Date: Sep. 16, 1997

[87] PCT Pub. No.: WO97/20517

PCT Pub. Date: Jun. 12, 1997

[30] Foreign Application Priority Data

Apr. 12, 1995 [GB] United Kingdom ............ 9524733

[51] Int. Cl.[7] ............ A61C 13/02; A61C 13/28
[52] U.S. Cl. ............ 433/168.1; 433/169
[58] Field of Search ............ 433/167, 168.1, 433/169, 170

[56] References Cited

U.S. PATENT DOCUMENTS

| | | | |
|---|---|---|---|
| 1,219,019 | 3/1917 | Magnus | 433/169 |
| 2,420,570 | 5/1947 | Shapiro | 433/169 |
| 2,473,515 | 6/1949 | Egger | 433/169 |
| 3,197,866 | 8/1965 | Barron | 433/169 |
| 3,785,054 | 1/1974 | Van Handel | 433/168.1 |
| 4,634,381 | 1/1987 | Kusano et al. | 433/168.1 |

*Primary Examiner*—Nicholas D. Lucchesi
*Attorney, Agent, or Firm*—Eric Fincham

[57] ABSTRACT

A resilient connecting structure for individually and resiliently connecting a dental prosthesis structure to a base component. The connecting structure is adapted to simulate the link provided by a natural periodontal ligament between a natural tooth and a natural healthy gum. The connecting structure thus allows individual three-dimentional freedom of pivotal movement about the base of the prosthesis structure, including rotation about a longitudinal axis of the latter. In one embodiment of the invention, the connecting structure is incorporated in an artificial dental structure that also includes the dental prosthesis and the base component. The dental prosthesis has dental body defining a crown section, a neck section and a root section. The base component has at least one base recess formed therein for receiving a section of said dental prosthesis. The connecting structure includes a membrane made of a resilient membrane material. The membrane is mounted on said root section of said dental prosthesis. The resilient membrane material and said membrane thickness are such that when said root section with said membrane mounted thereon are fittingly inserted in said base recess, said membrane allows said prosthesis structure to move from a first position to a second position in response to a pressure applied thereon and said membrane resiliently biases said prosthesis structure from said second position to said first position when said pressure is released. The resilient characteristics of the membrane material allows the membrane to recover its shape and size after deformation caused by the mechanical stress generated during the chewing process. The resilient characteristics of the membrane material thus allow the prosthesis structure on which it is mounted to spring back to its original position once the stress is released. The membrane could either be manufactured separately, mounted on the prosthesis structure at the manufacturing site or even mounted to both the prosthesis structure and the base component at the manufacturing site.

15 Claims, 6 Drawing Sheets

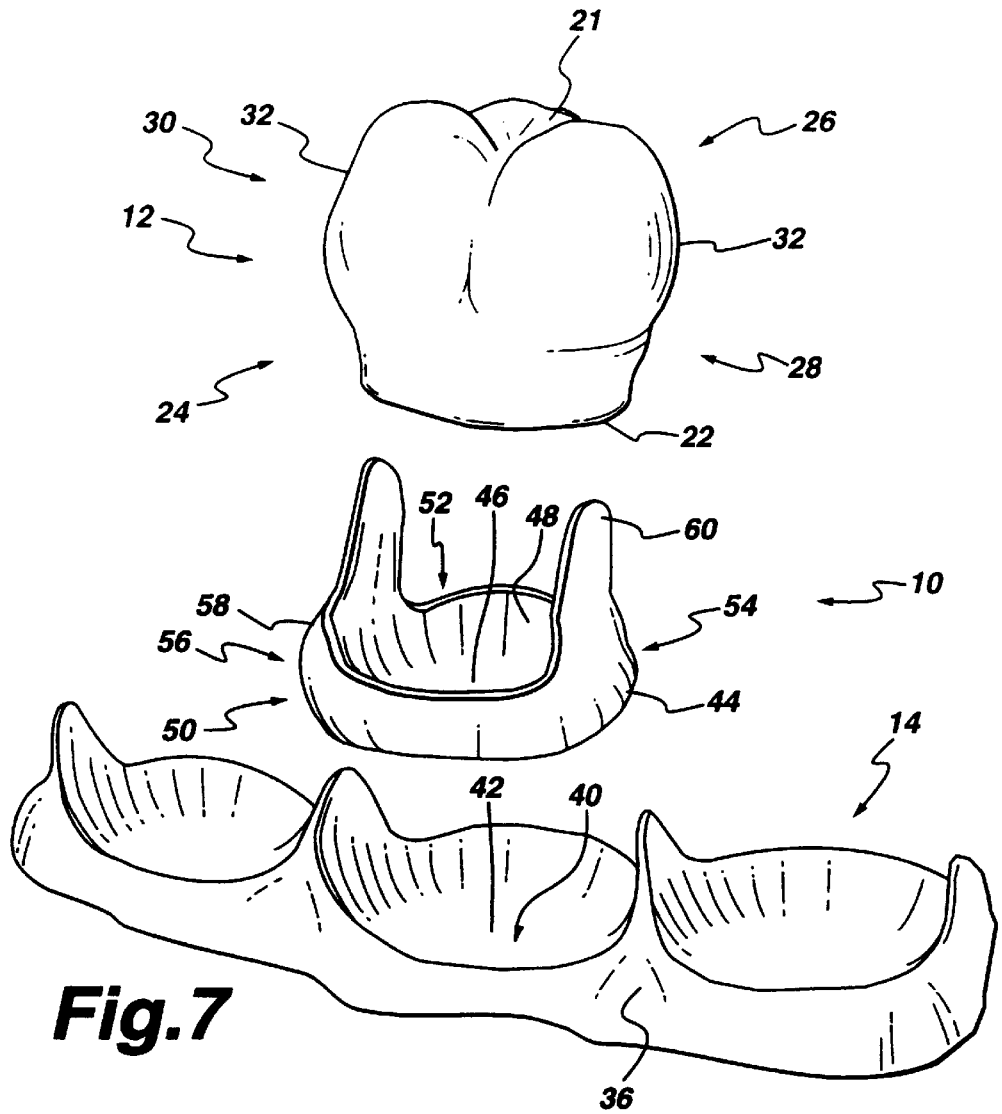
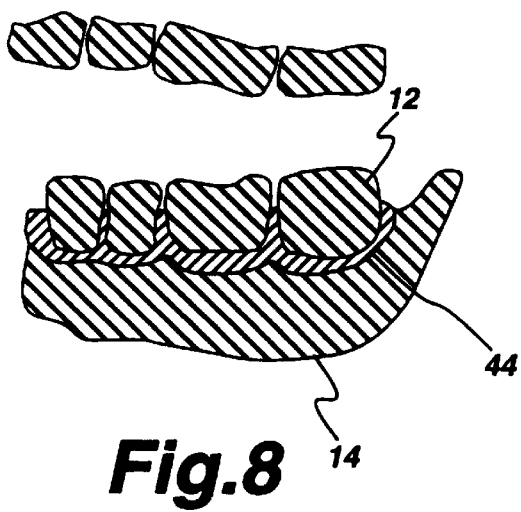
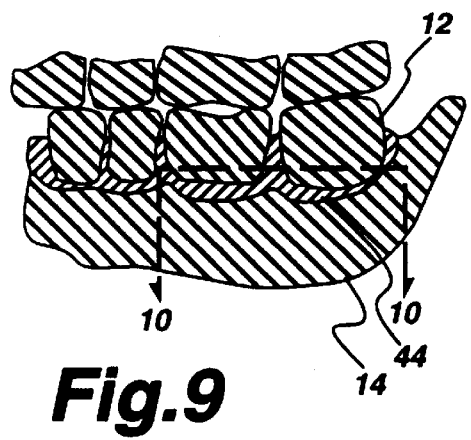
Fig.7
Fig.8
Fig.9

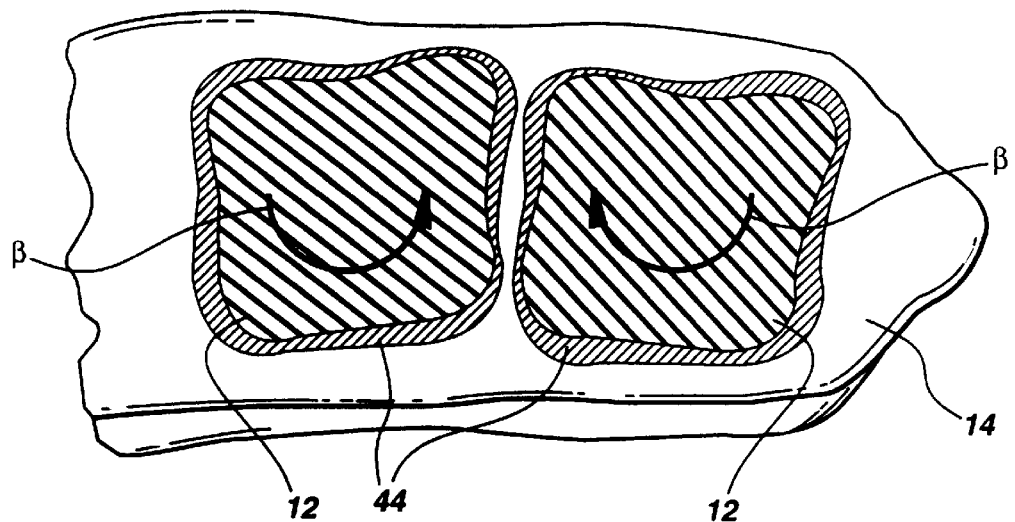
Fig. 10
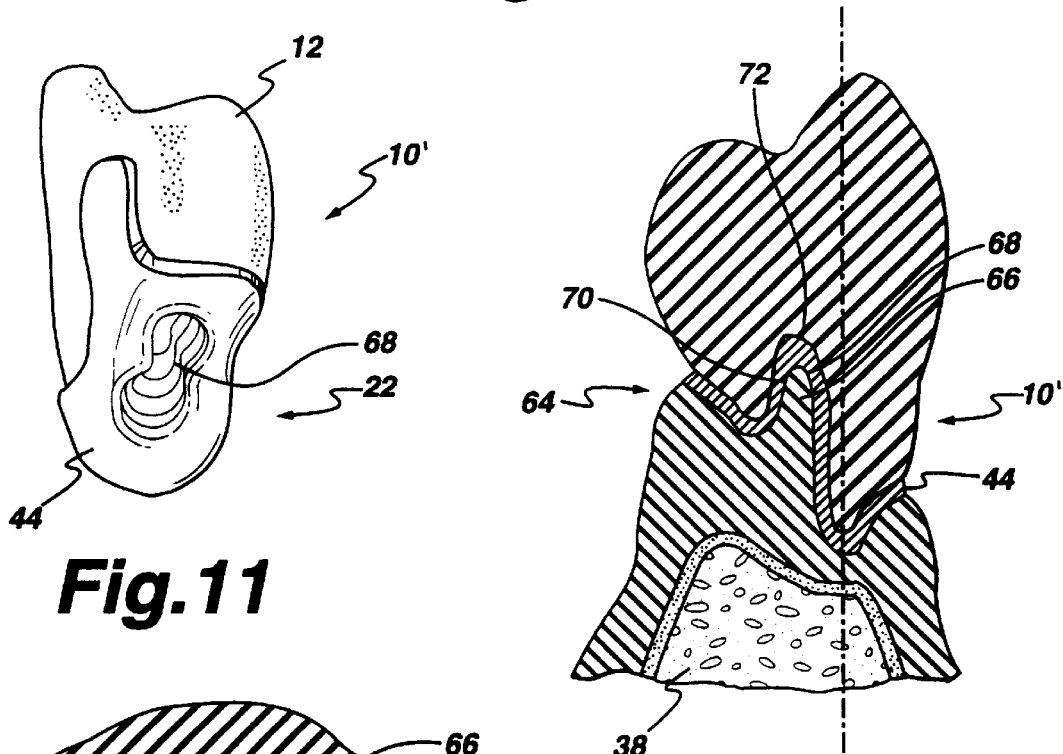
Fig. 11
Fig. 12
Fig. 13

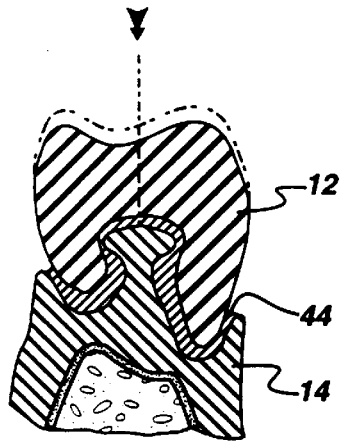 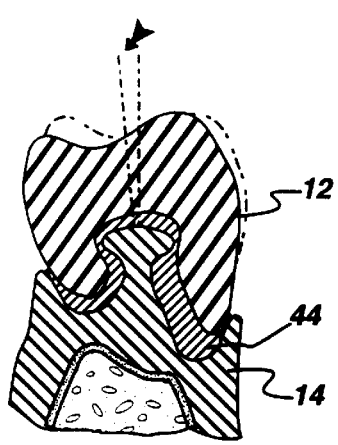 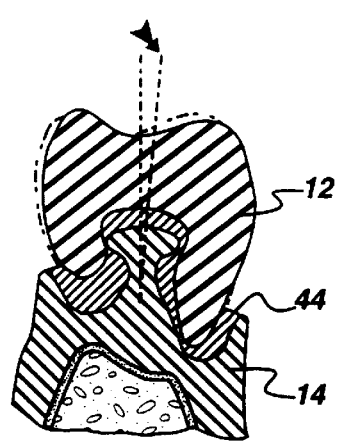
Fig. 14   Fig. 15   Fig. 16
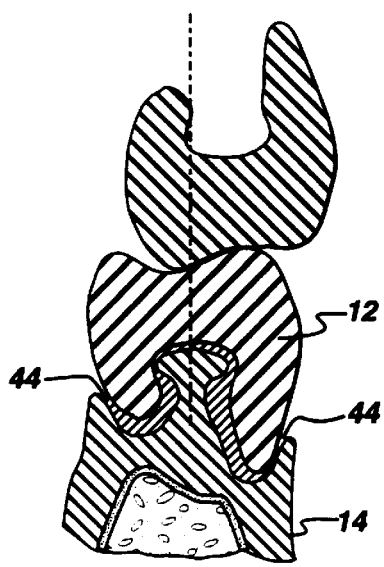
Fig. 17

RESILIENT DENTAL PROSTHESIS CONNECTING STRUCTURE

FIELD OF THE INVENTION

The present invention relates to the field of dental prosthesis structures and is particularly concerned with a resilient connecting structure for individually and resiliently connecting a dental prosthesis structure to a base component.

BACKGROUND OF THE INVENTION:

The field of dental prosthesis structures is replete with various types of connections for connecting a dental prosthesis to a base component in order to form an artificial dental structure. Some of the prior art structures provide a fixed connection between the dental prosthesis and the base component. Because of the rigidity of the assembly, such prior art structures have proven to be particularly susceptible to wear and are also quite uncomfortable for the intended patient.

Accordingly, there has been an effort towards providing an artificial dental structure incorporating some resilient component. One example of such prior art structure is disclosed in U.S. Pat. No. 5,098,295 naming Walter Durr and Axel Kirsch as inventors and issued Mar. 24, 1992. U.S. Pat. No. 5,098,295 discloses a plug connection for the detachable fitting of a prosthesis structure that includes a bearing ring in the cavity of an elastic material for relieving impact stresses occurring substantially in the direction of a longitudinal axis of symmetry of the post.

While the patent recognizes the need for a reduction of the impact stresses generated on the dental prosthesis, the structure disclosed in the document nevertheless suffers from a set of drawbacks. First, the structure only allows for a relative movement between the dental prosthesis and the tooth peg in the direction of a longitudinal axis of symmetry of the peg. Second, the structure does not allow for the individual movement of the dental prosthesis since all the dental prosthesis structures are rigidly mounted on a common rail acting as a base component.

Accordingly, there exists a need for an improved connecting structure.

SUMMARY OF THE INVENTION

It is an object of the present invention to provide an improved connecting structure for connecting a dental prosthesis structure to a base component.

In accordance with a first aspect of the invention, there is provided a connecting structure for connecting a dental prosthesis to a base component, the dental prosthesis defining a crown section, a neck section and a root section, the base component having at least one base recess formed therein for receiving the root section: the connecting structure comprising a membrane made of a resilient membrane material; the membrane being configured and sized so as to be fittingly mountable over the root section of the dental prosthesis; the membrane having a membrane thickness; the resilient membrane material and the membrane thickness being such that when the root section with the membrane mounted thereon are fittingly inserted in the base recess, the membrane allows the prosthesis structure to move from a first position to a second position in response to a pressure applied thereon and the membrane resiliently biases the prosthesis structure from the second position to the first position when the pressure is released.

Preferably, the membrane material is an elastomeric having a Young Modulus between 0.2 and 2.5 MPa and a shore hardness coefficient between 25% and 75%, and is an hydrophobic material.

Conveniently, the membrane material is chosen from a group of elastomeric resin including polysulfide organic rubbers, first generation siliconed elastomeric resins, second generation elastomeric resins and elastomeric polyethers.

Preferably, the membrane thickness has a value substantially in the range of between 0.1 mm and 1.5 mm.

Conveniently, the membrane defines a membrane bottom wall and a membrane peripheral wall; the membrane peripheral wall defining a peripheral wall oral segment and an opposed peripheral wall lingual segment; the membrane peripheral wall also defining a peripheral wall medial segment and an opposed peripheral wall distal segment; the peripheral wall further defining a peripheral wall upper peripheral edge positioned opposite the membrane base wall; the portion of the upper peripheral edge extending along the medial segment and the distal segment being located at a greater distance from the membrane base wall than the portion of the upper peripheral edge extending along the peripheral wall oral segment and the peripheral wall lingual segment; the peripheral wall medial segment and the peripheral wall distal segment thus each defining an integrally projecting tongue that projects generally away from the membrane base wall.

Preferably, the prosthesis structure defines an occlusal surface and an opposite base surface the prosthesis structure also defining a peripheral surface divided into a oral surface, a lingual surface, a medial surface and opposed distal surface; the crown section defining a pair of substantially opposed interproximal locations; the oral segment and the lingual segment both being configured and sized so as to be attachable correspondingly to the oral surface and the lingual surface part of the prosthesis structure; the oral segment and the lingual segment being adapted to extend from the base surface to the neck section of the prosthesis structure; the medial segment and the distal segment being both configured and sized so as to be attachable correspondingly to the medial surface and the distal surface part of the prosthesis structure; the medial segment and the distal segment being adapted to extend from the base surface to the interproximal locations.

In accordance with a second aspect of the invention, there is provided a dental prosthesis having a connecting structure for connecting the dental prosthesis to a base component, the base component having at least one base recess formed therein for receiving a section of the dental prosthesis, the dental prosthesis comprising a dental body defining a crown section, a neck section and a root section; a membrane made of a resilient membrane material; the membrane being mounted on the root section of the dental prosthesis; the membrane having a membrane thickness; the resilient membrane material and the membrane thickness being such that when the root section with the membrane mounted thereon are fittingly inserted in the base recess, the membrane allows the prosthesis structure to move from a first position to a second position in response to a pressure applied thereon and the membrane resiliently biases the prosthesis structure from the second position to the first position when the pressure is released.

In one embodiment of the invention, the dental prosthesis further includes a prosthesis recess formed in the base surface and the membrane further includes a recess lining section that extends integrally from the adjacent sections of the membrane so as to line the inner surface of the prosthesis recess.

In accordance with a third aspect of the invention, there is provided an artificial dental structure for an intended patient having a natural gum, the artificial dental structure comprising a dental prosthesis, the dental prosthesis having a dental body defining a crown section, a neck section and a root section; a base component for mounting the artificial dental structure on the gum, the base component having at least one base recess formed therein for receiving a section of the dental prosthesis; a connecting structure for connecting the dental prosthesis to the base component, the connecting structure including a membrane made of a resilient membrane material; the membrane being mounted on the root section of the dental prosthesis; the membrane having a membrane thickness; the resilient membrane material and the membrane thickness being such that when the root section with the membrane mounted thereon are fittingly inserted in the base recess, the membrane allows the prosthesis structure to move from a first position to a second position in response to a pressure applied thereon and the membrane resiliently biases the prosthesis structure from the second position to the first position when the pressure is released.

In one embodiment of the invention, each base recess defines a recess base wall and an integrally extending recess peripheral wall, the base component further including a stabilizing pin that extend integrally from the recess base wall; the dental prosthesis further including a prosthesis recess formed in the base surface and the membrane further includes a recess lining section that extends integrally from the adjacent sections of the membrane so as to line the inner surface of the prosthesis recess; the prosthesis recess and the recess lining section being configured and sized so as to fittingly receive the stabilizing pin; whereby the stabilizing pin is adapted to act as a stabilizing means, in cooperation with the recess peripheral wall for abuttingly limiting the relative range of motion between the prosthesis structure and the base member.

Preferably, the stabilizing pin has a conical general configuration, the conical configuration defining an apex, the apex having a generally dome shaped configuration.

Conveniently, the stabilizing pin has a generally "8"-shaped transversal cross-sectional configuration and a generally "T"-shaped longitudinal cross-sectional configuration.

In accordance with yet another embodiment of the invention, the prosthesis structure further includes an anchoring lip that extends integrally and substantially outwardly from the lingual surface of the prosthesis structure adjacent the base surface; the membrane being configured and sized so as to be in an overlapping relationship relatively to the anchoring lip.

Conveniently, the anchoring lip extends across the lingual surface and the anchoring lip has a slightly curved cross-sectional configuration with the tip of the anchoring lip turning towards the occlusal surface.

Advantages of the present invention include that the connecting structure allows for an individual movement of the prosthesis structure to which it is attached relatively to a base component on which the prosthesis structure is mounted.

Another advantage of the present invention resides in that the connecting structure allows for a variety of relative movements between the prosthesis structure and the base component including a translational movement of the prosthesis structure along its longitudinal axis, a three-dimensional tilting movement of the prosthesis structure about its root relatively to the base component and a rotational movement of the prosthesis structure relatively to the base component about the longitudinal axis of the prosthesis structure. The variety of allowed movements, in turn, allows for a relatively large trituration surface on the prosthesis structure.

A further advantage of the present invention resides in the resilient characteristics of the connecting structure.

Another advantage of the present invention resides in that the connecting structure simulates the link provided by a natural periodontal ligament between a natural tooth and a natural healthy gum.

A still further advantage of the present invention resides in that the connecting structure in accordance with the present invention will conform to conventional forms of manufacturing, be of simple construction and easy to use so as to provide a connecting structure that will be economically feasible, long lasting and relatively trouble free in operation.

BRIEF DESCRIPTION OF THE DRAWINGS

Various embodiments of the present invention will now be described, by way of example, in reference to the following drawings in which:

FIG. 7: in an exploded view, illustrates a connecting structure in accordance with the first embodiment of the present invention, the connecting structure being used for connecting a prosthesis structure to a base component;

FIG. 8: in a longitudinal cross-sectional view, illustrates a set of prosthesis structures, each prosthesis structure being mounted on a base component by a connecting structure in accordance with a first embodiment of the present invention, the prosthesis structures being shown about to be compressed by a set of teeth;

FIG. 9: in a longitudinal cross-sectional view, illustrates a set of prosthesis structures, each prosthesis structure being mounted on a base component by a connecting structure in accordance with a first embodiment of the present invention, the prosthesis structures being shown compressed by a set of teeth;

FIG. 10: in a transversal cross-sectional view taken along arrows 10—10 of FIG. 9, illustrates a pair of prosthesis structures, each prosthesis structure being mounted on a base component using a connecting structure in accordance with a first embodiment of the present invention, the prosthesis structures being shown in a pivoted relationship relatively to the base component;

FIG. 11: in a rear bottom perspective view, illustrates a resilient membrane part of a connecting structure in accordance with a second embodiment of the present invention, the membrane being mounted on a prosthesis structure;

FIG. 12: in a cross-sectional view, illustrates a prosthesis structure mounted on a base component using a connecting structure in accordance with a second embodiment of the present invention;

FIG. 13: in a transversal cross-sectional view, illustrates a prosthesis structure mounted on a base component using a connecting structure in accordance with a second embodiment of the present invention, the prosthesis structure being shown in a pivoted relationship relatively to the base component;

FIG. 14: in a longitudinal cross-sectional view, illustrates a prosthesis structure mounted on a base component using a connecting structure in accordance with a third embodiment of the present invention, the prosthesis structure being biased by a force acting along its longitudinal axis;

FIG. 15: in a longitudinal cross-sectional view, illustrates a prosthesis structure mounted on a base component by a connecting structure in accordance with a third embodiment of the present invention, the prosthesis structure being shown with a leftward tilting force acting upon it;

FIG. 16: in a longitudinal cross-sectional view, illustrates a prosthesis structure mounted on a base component by a connecting structure in accordance with a third embodiment of the present invention, the prosthesis structure being shown with a rightward tilting force acting upon it;

FIG. 17: in a longitudinal cross-sectional view, illustrates a prosthesis structure mounted on a base component by a connecting structure in accordance with a third embodiment of the present invention, the prosthesis structure being shown compressed by an opposed tooth;

DETAILED DESCRIPTION

Figure 1:
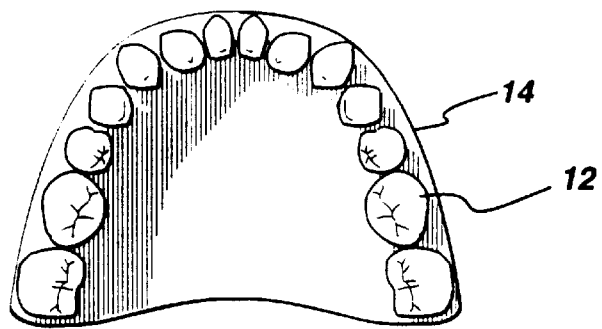
FIG. 1: in a planar view, illustrates a set of prosthesis structures mounted on a base component using a connecting structure in accordance with an embodiment of the present invention.
Figure 2:
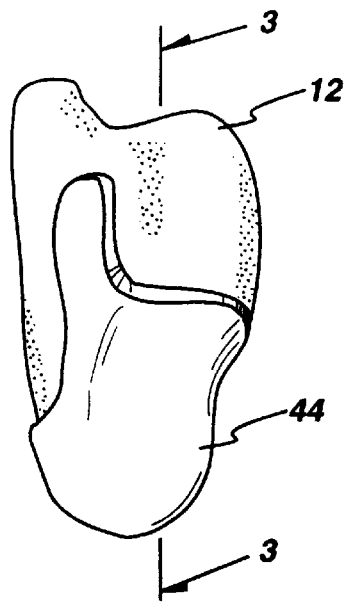
FIG. 2: in an elevational view, illustrates a resilient membrane part of a connecting structure in accordance with an embodiment of the present invention, the membrane being mounted on a conventional prosthesis structure.
Figure 3:
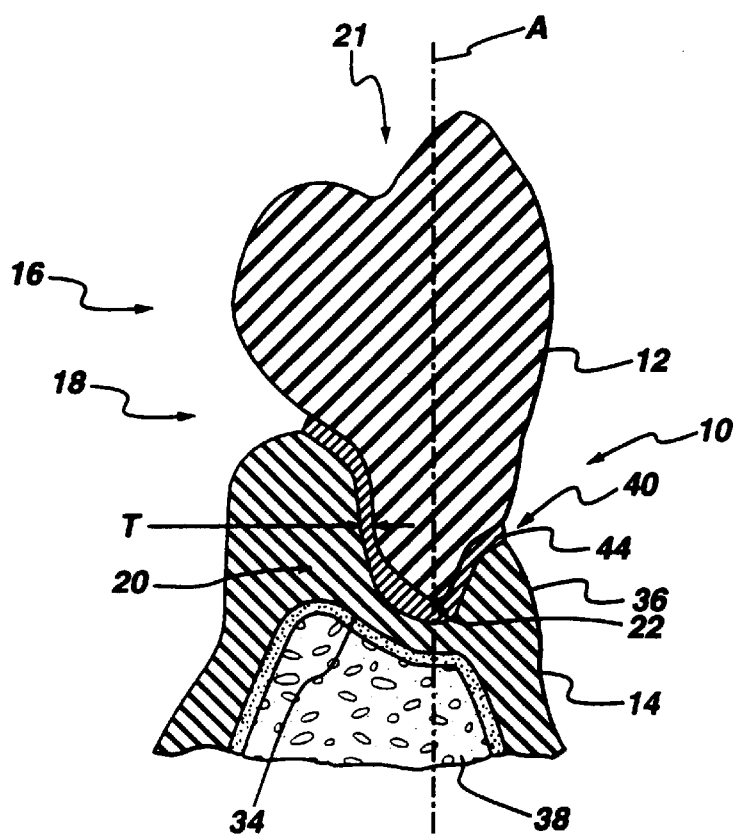
FIG. 3: in a cross-sectional view taken along arrows 3—3 of FIG. 2, illustrates a prosthesis structure mounted on a base component using a connecting structure in accordance with a first embodiment of the present invention.

Referring to FIG. 3, there is shown a resilient connecting structure 10 in accordance with a first embodiment of the present invention. The connecting structure 10 is shown resiliently connecting a prosthesis structure 12 such as an artificial tooth to a supporting base component 14 such as an artificial gum, a dental rail, or the like.

Typically, the prosthesis structure 12 defines a crown section 16, a neck section 18 and a root section 20. The crown section 16 is preferably configured so as to simulate the crown section of a real tooth. The prosthesis structure 12 defines a longitudinal axis A extending longitudinally therethrough, from the root section 20 to the crown section 16.

As we will hereinafter disclose, the root section 20 is adapted to be inserted into the base component 14. The neck section 18 forms a transitional section between the crown section 16 and root section 20. The neck section 18 of the prosthesis structure 12 is adapted to simulate the neck section of a real tooth. As with a real tooth and a real gum, the neck section 18 follows the upper surface of the base member 14 in which the prosthesis structure 12 is inserted As with a real tooth, the prosthesis structure 12 defines an occlusal surface 21 and an opposite base surface 22. As illustrated more specifically in FIG. 7, the prosthesis structure 12 also defines a peripheral surface divided into an oral surface 24, a lingual surface 26, a medial surface 28 and opposed distal surface 30.

The crown section 16 preferably defines a pair of substantially opposed interproximal locations 32. As with a real tooth, the interproximal locations 32 correspond to an ideal contact location between the medial and distal surfaces of adjacent teeth.

The base component 14 includes a strip of substantially rigid material such as acrylic or the like. As illustrated more specifically in FIG. 3, the base component 14 includes a base internal surface 34 and base exterior surface 36.

The base component 14 preferably has a generally "U" shaped cross-sectional configuration so as to be fittingly insertable over the natural gum 38 of the intended patient. The base exterior surface 36 has at least one base recess 40 formed therein. Each base recess 40 is configured and sized so as to fittingly receive the root section 20 of a corresponding prosthesis structure 12 and a corresponding connecting structure 10.

As illustrated in FIG. 7, each base recess 40 defines a recess base wall 42 and an integrally extending recess peripheral wall 44. It should be understood that the general configuration of the prosthesis structure 12 and of the base component 14 could vary without departing from the scope of the present invention.

The connecting structure 10 includes a membrane 44 made of a substantially resiliently material herein referred to as the membrane material. The resilient characteristic of the membrane material allows the membrane 44 to recover its shape and size after deformation caused by the mechanical stress generated during the chewing process. The resilient characteristics of the membrane material thus allow the prosthesis structure 12 on which it is mounted to spring back to its original position once the stress is released.

The membrane 44 has a thickness indicated by the reference character "T" in FIG. 3. The thickness "T" of the membrane 44 is customized for a given material so that the combination of the thickness and of the specific mechanical properties of the material allow the membrane 44 to simulate the resilient characteristics of the periodontal ligament of a natural tooth. The membrane 44 thus allows each prosthesis structure 12 to move independently relatively to the base component 14 in a manner similar to the individual movements of a natural tooth relatively to a healthy natural gum.

Typically, when the membrane material is an elastomeric resin, the membrane 44 has a thickness substantially in the range between 0.1 mm and 1.5 mm. The thickness "T" of the membrane 44 is preferably kept at low values so as to reduce the external surface of the membrane 44 in contact with the oral environment. Since most elastomeric resins are relatively porous, the relatively small external surface in contact with the oral environment reduces the risk of creating a focus of bacterial proliferation.

To further reduce the risk of bacterial proliferation, the membrane material is chosen so as to also exhibits hydrophobic properties. The membrane material also preferably exhibits long term high dimensional stability so as to enhance the predictability of the positioning of the prosthesis structure 12 relatively to the base structure 14.

Typically, the membrane material has a Young Modulus between 0.2 and 2.5 MPa and a Shore hardness coefficient between 25% and 75%. The membrane material is preferably chosen from a group of elastomeric resins including polysulfide organic rubber, first or second generation siliconed elastomeric resins or elastomeric polyethers.

It should be understood that the type of membrane material could vary without departing from the scope of the present invention as long it allows for a resilient connection between the prosthesis structure 12 and the base component 14. Preferably, the resilient connection simulates the mechanical properties of a periodontal ligament extending between a natural tooth and a natural healthy gum.

As illustrated more specifically in FIG. 7, the membrane 44 defines a membrane bottom wall 46 and a membrane peripheral wall 49. The membrane peripheral wall 48, in turn, defines a peripheral wall oral segment 50 and an opposed peripheral wall lingual segment 52. The membrane peripheral wall 48 also defines a peripheral wall medial segment 54 and an opposed peripheral wall distal segment 56. The peripheral wall 48 further defines a peripheral wall upper peripheral edge 58 positioned opposite the membrane base wall 46.

The upper peripheral edge 58 of the medial segment 54 and of the distal segment 56 is located at a greater distance from the membrane base wall 46 than the portion of the upper peripheral edge 58 part of the peripheral wall oral segment 50 and the peripheral wall lingual segment 52. The peripheral wall medial segment 54 and the peripheral wall distal segment 56 thus each define an integrally projecting tongue 60 that projects generally away from the membrane base wall 46. The tongues 60 are adapted to simulate the papillas of a natural gum.

The oral segment 50 and the lingual segment 52 are configured and sized so as to be attached correspondingly to the oral surface 24 and lingual surface 26 of the prosthesis structure 12. The oral segment 50 and the lingual segment 52 are adapted to extend from the base surface 22 to the neck section 18 of the prosthesis structure 12. The medial segment 54 and the distal segment 56 are configured and sized so as to be attached correspondingly to the medial surface 28 and the distal surface 30 of the prosthesis structure 12. The medial segment 54 and the distal segment 56 are adapted to extend from the base surface 22 to the interproximal locations 32.

Figure 4:
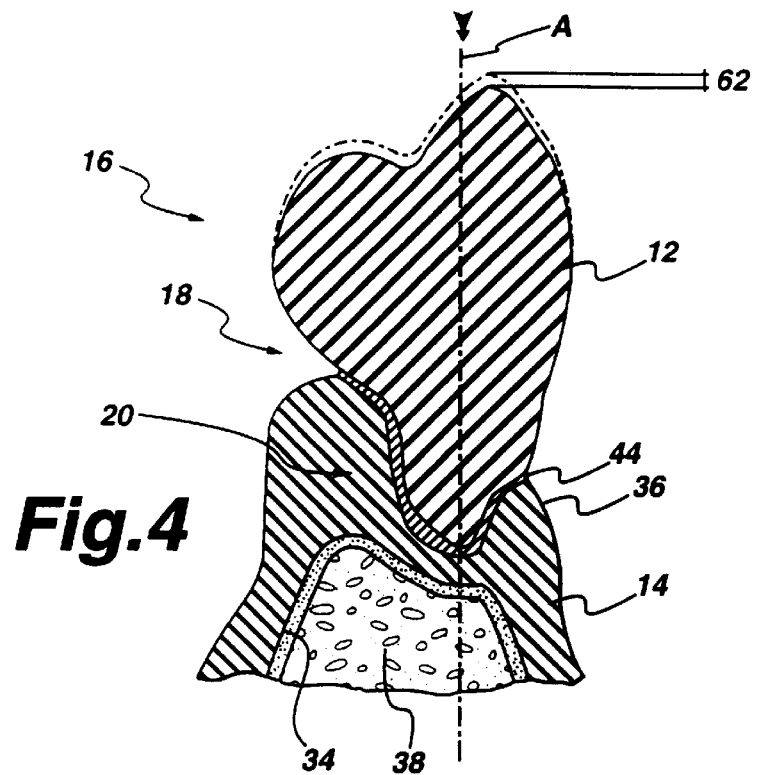
FIG. 4: in a longitudinal cross-sectional view, illustrates a prosthesis structure mounted on a base component using a connecting structure in accordance with a first embodiment of the present invention, the prosthesis structure being biased by a force acting along its longitudinal axis.
Figures 5, 6:
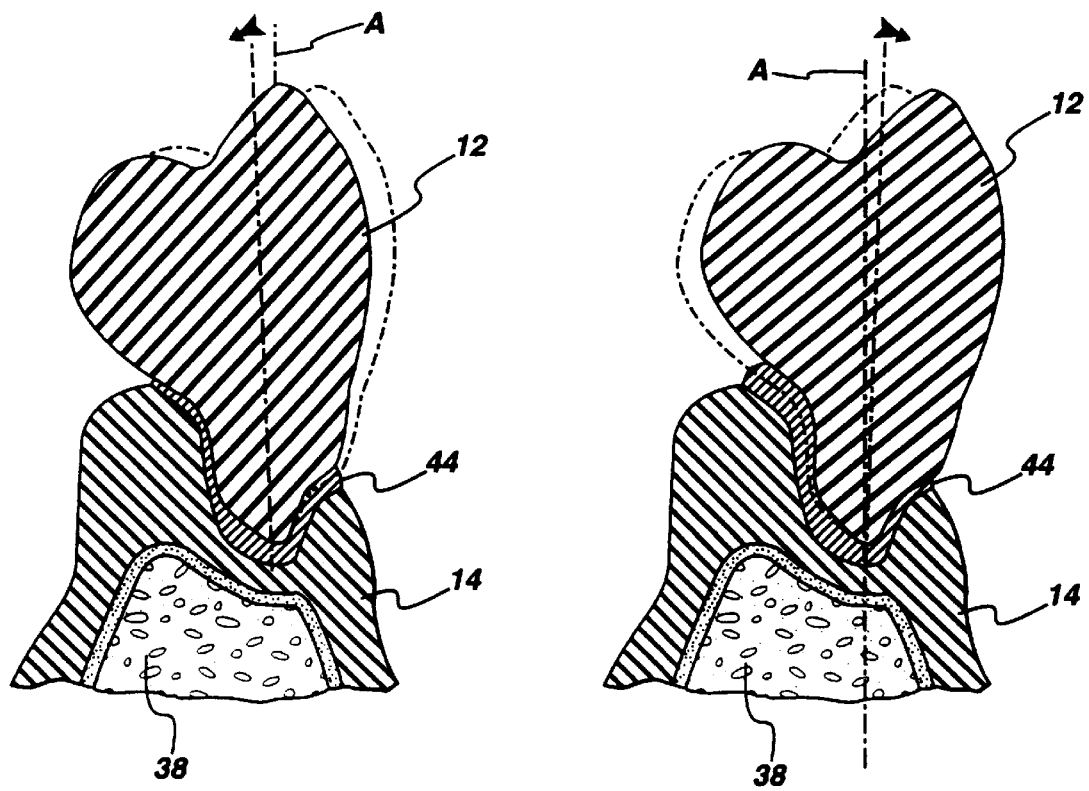
FIG. 5: in a longitudinal cross-sectional view, illustrates a prosthesis structure mounted on a base component by a connecting structure in accordance with a first embodiment of the present invention, the prosthesis structure being shown with a leftward tilting force acting upon it.
FIG. 6: in a longitudinal cross-sectional view, illustrates a prosthesis structure mounted on a base component by a connecting structure in accordance with a first embodiment of the present invention, the prosthesis structure being shown with a rightward tilting force acting upon it.

As illustrated in FIGS. 4 through 6 and in FIG. 10, the membrane 44 is adapted to allow an individual and resilient relative movement between each prosthesis structure 12 and the base component 14.

FIG. 4 illustrates a situation wherein a compressive force is applied on the prosthesis structure 12 along the longitudinal axis A. As illustrated, the membrane 44 allows for a translational displacement 62 in the direction of the longitudinal axis A.

Typically, the thickness of membrane 44 and the mechanical properties of the membrane material are chosen so as to allow for a translational displacement 62 substantially in the range of 0.25 mm and 1 mm. The thickness of the membrane 44 and the mechanical properties of the membrane material are chosen so that when the compressive force is released the prosthesis structure 12 is resiliently biased towards its original position by the resilient characteristics of the membrane 44.

FIGS. 5 and 6 illustrate, in a similar manner, a pair of opposed tilting movements of the prosthesis structure 12 wherein the longitudinal axis A is respectively tilted towards a lingual and an oral direction relatively to the base member 14. Again, the thickness of the membrane 44 and the mechanical properties of the membrane material are chosen so as to allow for a tilting relative displacement between the prosthesis structure 12 and the base component 14 compatible with the relative displacement between a real tooth and a real healthy gum.

Also, the thickness of the membrane 44 and the mechanical properties of the membrane material are chosen so that when the compressive force is released, the prosthesis structure 12 is resiliently biased towards its original position.

As illustrated in FIG. 10, one of the main features of the present invention reside in that the membrane 44 not only allows for a translational movement of the prosthesis structure 12 along the longitudinal axis A and a tilting displacement of the prosthesis structure 12 relatively to the base member 14 but the membrane 44 also allows for an individual and resilient rotational movement of each prosthesis structure 12 relatively to the base component 14 about their corresponding longitudinal axis A, as indicated by arrow B.

Again, the thickness of the membrane 44 and the mechanical properties of the membrane material are chosen so that the rotational movement of each prosthesis structure 12 about its corresponding longitudinal axis A simulates the behavior of a tooth rotating about its longitudinal axis when the latter is attached to a healthy gum by a periodontal ligament.

It should be understood that although FIGS. 4 through 6 and FIG. 10 only illustrate translational, tilting and rotational relative displacement between individual prosthesis structures 12 and the base component 14, the membrane 44 allows for any individual or combination of three-dimensional relative displacements between individual prosthesis structures 12 and the base component 14 that simulates the relative displacement between a real tooth and a healthy gum.

As illustrated in FIGS. 8 and 9, each individual prosthesis structure 12 being individually and resiliently secured to the base component 14, the prosthesis structure 12 are allowed to move in opposite directions when they are contacted by corresponding prosthesis structures or real tooth mounted on the opposite jaw of the intended patient. This type of behavior simulates the behavior of natural teeth anchored inside the healthy gum and allows for a relatively large trituration surface compared to the trituration surface of conventional dental prosthesis.

FIGS. 11 through 18, illustrate a resilient connecting structure 10' in accordance with a second embodiment of the present invention. The connecting structure 10' is substantially similar to the connecting structure 10 making up the first embodiment. The main difference between the first and second embodiments of the present invention resides in the presence of a stabilizing structure 64 for stabilizing each individual prosthesis structure 12.

Each stabilizing structure 64 includes a stabilizing pin 66 that extend integrally from a corresponding recess base wall 42. Each stabilizing structure 64 also includes a prosthesis recess 68 formed in the base surface 22 of each prosthesis structure 12. Each stabilizing structure 64 further includes a recess lining section 70 that extends integrally from the adjacent sections of the membrane 44 so as to line the inner surface of the prosthesis recess 68.

Each prosthesis recess 68 and its corresponding recess lining section 70 is configured and sized so as to fittingly receive a corresponding stabilizing pin 66 part of a corresponding stabilizing structure 64. Each stabilizing structure 64 is adapted to act as a stabilizing means, in cooperation with the recess peripheral wall 44 for abuttingly limiting the relative range of motion between the prosthesis structure 12 and the base member 14.

Figure 18:
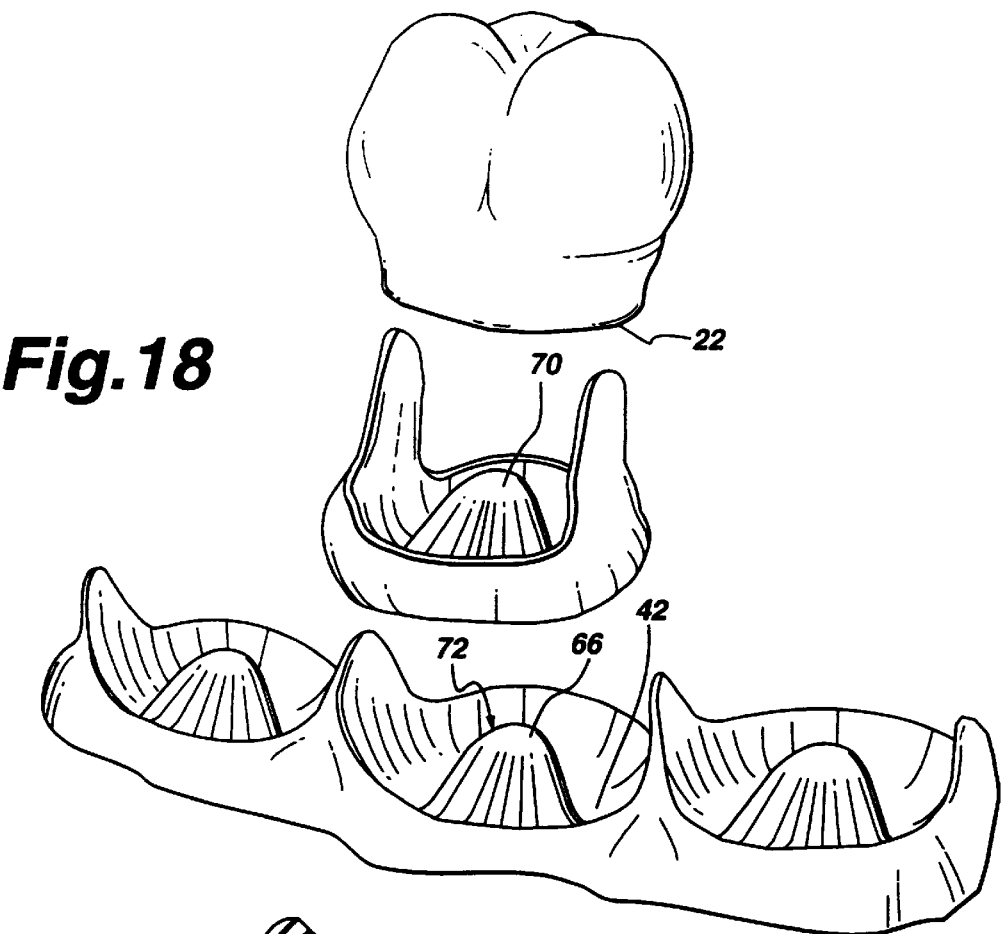
FIG. 18: in an exploded view, illustrates a connecting structure in accordance with a second embodiment of the present invention, the connecting structure being used for connecting a prosthesis structure to a base component.

Each stabilizing pin 66 and corresponding prosthesis recess 68 may have any suitable shape that allows for relative movements including a rotational relative movement of the prosthesis structure 12 relatively to the base member 14 about its longitudinal axis A. For example, as illustrated in FIGS. 12 and 18, the stabilizing pin 66 could have a cylindrical or conical general configuration. Preferably, the apex segment 72 of the stabilizing pin 66 has a generally dome shaped configuration so as to facilitate the tilting movement of the prosthesis structure 12 relatively to the base member 14.

In some situations, it is desirable to configure the stabilizing pin 66 and the corresponding prosthesis recess 68 so that the latter structures abuttingly limit the range of motion in a first predetermined set of direction while allowing a greater range of motion in a second predetermined set of directions. For example, FIGS. 14 through 16 illustrate a specific configuration wherein the stabilizing pin 66 has a generally "8" shaped transversal cross-sectional configuration (similar to that shown in FIG. 13) and a generally "T"-shaped vertical cross-sectional configuration.

The specific configuration of the stabilizing pin illustrated in FIGS. 14 through 16 allows for a relatively limited rotational movement of the prosthesis structure about its longitudinal axis A and a relatively limited range of tilting motion while allowing a relatively large range of translational motion in a direction parallel to the longitudinal axis A. The configuration of the stabilizing pin 66 thus allows for the customization of the predetermined range of motions.

It should be noted that the configuration of the pin 66 allows for a customization that is independent of the thickness of the membrane 44. The thickness of the membrane 44 can thus remain constant. The constant thickness of the membrane 44, in turn, facilitates the manufacturing process. It should be understood that the customization of the range of motion in predetermined directions could be attained using other methods such as by varying the thickness of the membrane 44 without departing from the scope of the present invention.

Figure 19:
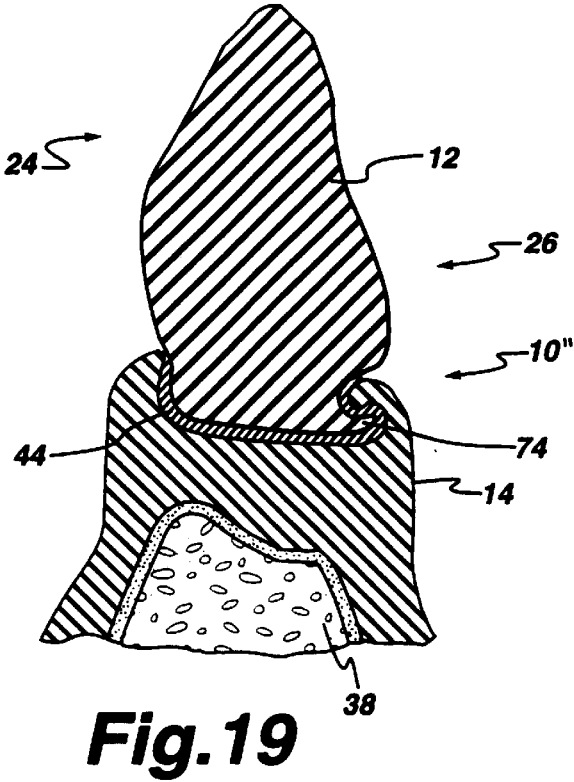
FIG. 19: in a longitudinal cross-sectional view, illustrates a prosthesis structure mounted on a base component by a connecting structure in accordance with a fourth embodiment of the present invention.
Figure 20:
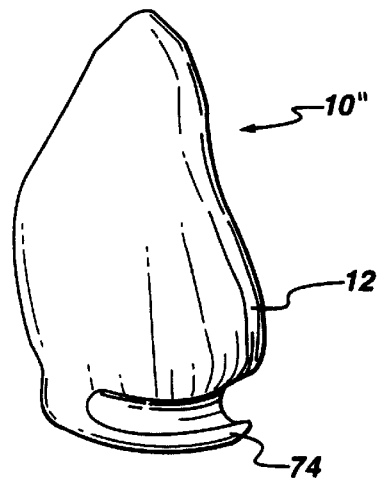
FIG. 20: in an elevational view, illustrates a prosthesis structure part of a connecting structure in accordance with a fourth embodiment of the present invention.

FIGS. 19 and 20 illustrate a dental prosthesis having a connecting structure 10" in accordance with a fourth embodiment of the present invention. The connecting structure 10" is particularly suited for situations wherein the prosthesis structure 12 is subjected to relatively large tilting pressures that tend to bias the occlusal surface 21 of the prosthesis structure towards the lingual side. The connecting structure 10" is thus particularly suited for prosthesis structures 12 that are adapted to act as incisors.

The fourth embodiment of the invention is substantially similar to the first three embodiments except for the presence of an anchoring lip 74 that extends integrally and substantially outwardly from the lingual surface 26 of the prosthesis structure 12 adjacent the base surface 22. Preferably, the anchoring lip 74 extends across the lingual surface 26. Preferably, the anchoring lip 74 has a slightly curved cross-sectional configuration with the tip of the anchoring lip 74 turning towards the occlusal surface 21.

As illustrated in FIG. 19, the membrane 44 is configured and sized so as to be in an overlapping relationship relatively to the anchoring lip 74. In use, both the anchoring lip 74 and the membrane 44 are adapted to be mounted in the base member 14.

The membrane 44 could either be manufactured separately, mounted on the prosthesis structure 12 at the manufacturing site or even mounted to both the prosthesis structure 12 and the base component 14 at the manufacturing site. Typically, the membrane 44 is mounted on the prosthesis structure 12 at the manufacturing site and the base component 14 is customized for the given combination of prosthesis structure 12 and membrane 44 by a denturologist or any other skilled workmen. The membrane 44 could be mounted on the prosthesis structure 12 using a layer of adhesive material, by heat shrinking, chemical bounding, by friction or any other suitable means without departing from the scope of the present invention.

The embodiments of the invention in which an exclusive privilege or property is claimed are defined as follows:

1. A dental structure for a patient having a gum, said dental structure comprising a dental prosthesis, a base component, and a connecting structure connecting said dental prosthesis to said base component, said dental prosthesis having a crown section, a neck section and a root section, said base component having at least one base recess formed therein for receiving said root section, said connecting structure comprising:

a membrane made of a resilient membrane material; said membrane being configured and sized so as to be fittingly mountable over said root section of said dental prosthesis; said membrane having a membrane thickness; said resilient membrane material and said membrane thickness being such that when said root section with said membrane mounted thereon are fittingly inserted in said base recess, said membrane allows said prosthesis structure to move from a first position to a second position in response to a pressure applied thereon and said membrane resiliently biases said prosthesis structure from said second position to said first position when said pressure is released, and wherein said membrane defines a membrane bottom wall and a membrane peripheral wall; said membrane peripheral wall defining a peripheral wall oral segment and an opposed peripheral wall lingual segment; said membrane peripheral wall also defining a peripheral wall medial segment and an opposed peripheral wall distal segment; said peripheral wall further defining a peripheral wall upper peripheral edge positioned opposite said membrane base wall; the portion of the upper peripheral edge extending along said medial segment and said distal segment being located at a greater distance from said membrane base wall than said portion of said upper peripheral edge extending along said peripheral wall oral segment and said peripheral wall lingual segment; said peripheral wall medial segment and said peripheral wall distal segment thus each defining an integrally projecting tongue that projects generally away from said membrane base wall.

2. A dental structure as recited in claim 1 wherein said membrane material is an elastomeric having a Young Modulus between 0.2 and 2.5 Mpa and a shore hardness coefficient between 25% and 75%.

3. A dental structure as recited in claim 2 wherein said membrane material is an hydrophobic material.

4. A dental structure as recited in claim 1 wherein said membrane material is chosen from a group of elastomeric resin including polysulfide organic rubbers, first generation siliconed elastomeric resins, second generation elastomeric resins and elastomeric polyethers.

5. A dental structure as recited in claim 1 wherein said membrane thickness has a value substantially in the range of between 0.1 mm and 1.5 mm.

6. A dental structure as recited in claim 1 wherein said prosthesis structure defines an occlusal surface and an opposite base surface said prosthesis structure also defining a peripheral surface divided into a oral surface, a lingual surface, a medial surface and opposed distal surface; said crown section defining a pair of substantially opposed interproximal locations; said oral segment and said lingual segment both being configured and sized so as to be attachable correspondingly to said oral surface and said lingual surface part of said prosthesis structure; said oral segment and said lingual segment being adapted to extend from said base surface to said neck section of said prosthesis structure; said medial segment and said distal segment being both configured and sized so as to be attachable correspondingly to said medial surface and said distal surface part of said prosthesis structure; said medial segment and said distal segment being adapted to extend from said base surface to said interproximal locations.

7. A dental prosthesis having a connecting structure for connecting said dental prosthesis to a base component, said base component having at least one base recess formed therein for receiving a section of said dental prosthesis, said dental prosthesis comprising:

a dental body defining a crown section, a neck section and a root section;

a membrane made of a resilient membrane material; said membrane being mounted on said root section of said dental prosthesis; said membrane having a membrane thickness; said resilient membrane material and said membrane thickness being such that when said root section with said membrane mounted thereon are fittingly inserted in said base recess, said membrane allows said prosthesis structure to move from a first position to a second position in response to a pressure applied thereon and said membrane resiliently biases said prosthesis structure from said second position to said first position when said pressure is released, said membrane defining a membrane bottom wall and a membrane peripheral wall; said membrane peripheral wall defining a peripheral wall oral segment and an opposed peripheral wall lingual segment; said membrane peripheral wall also defining a peripheral wall medial segment and an opposed peripheral wall distal segment; said peripheral wall further defining a peripheral wall upper peripheral edge positioned opposite said membrane base wall; the portion of the upper peripheral edge extending along said medial segment and said distal segment being located at a greater distance from said membrane base wall than said portion of said upper peripheral edge extending along said peripheral wall oral segment and said peripheral wall lingual segment; said peripheral wall medial segment and said peripheral wall distal segment thus each defining an integrally projecting tongue that projects generally away from said membrane base wall; said prosthesis structure defining an occlusal surface and an opposite base surface; said prosthesis structure also defining a peripheral surface divided into a oral surface, a lingual surface, a medial surface and opposed distal surface; said crown section defining a pair of substantially opposed interproximal locations; said oral segment and said lingual segment both being configured and sized so as to be attachable correspondingly to said oral surface and said lingual surface part of said prosthesis structure; said oral segment and said lingual segment being adapted to extend from said base surface to said neck section of said prosthesis structure; said medial segment and said distal segment being both configured and sized so as to be attachable correspondingly to said medial surface and said distal surface part of said prosthesis structure; said medial segment and said distal segment being adapted to extend from said base surface to said interproximal locations.

8. A dental prosthesis as recited in claim 7 wherein said dental prosthesis further includes a prosthesis recess formed in said base surface and said membrane further includes a recess lining section that extends integrally from said adjacent sections of said membrane so as to line the inner surface of said prosthesis recess.

9. A dental prosthesis as recited in claim 7 further comprising an anchoring lip that extends integrally and substantially outwardly from said lingual surface of said prosthesis structure adjacent said base surface; said membrane being configured and sized so as to be in an overlapping relationship relatively to said anchoring lip.

10. A dental prosthesis as recited in claim 9 wherein said anchoring lip extends across said lingual surface and said anchoring lip has a slightly curved cross-sectional configuration with said tip of said anchoring lip turning towards said occlusal surface.

11. An artificial dental structure for an intended patient having a gum, said artificial dental structure comprising:

a dental prosthesis, said dental prosthesis having a dental body defining a crown section, a neck section and a root section;

a base component for mounting aid artificial dental structure on said gum, said base component having at least one base recess formed therein for receiving a section of said dental prosthesis;

a connecting structure for connecting said dental prosthesis to said base component, said connecting structure including a membrane made of a resilient membrane material; said membrane being mounted on said root section of said dental prosthesis; said membrane having a membrane thickness; said resilient membrane material and said membrane thickness being such that when said root section with said membrane mounted thereon are fittingly inserted in said base recess, said membrane allows said prosthesis structure to move from a first position to a second position in response to a pressure applied thereon and said membrane resiliently biases said prosthesis structure from said second position to said first position when said pressure is released, and wherein each base recess defines a recess base wall and an integrally extending recess peripheral wall, said base component further including a stabilizing pin that extend integrally from said recess base wall; said dental prosthesis further including a prosthesis recess formed in said base surface and said membrane further includes a recess lining section that extends integrally from said adjacent sections of said membrane so as to line the inner surface of said prosthesis recess; said prosthesis recess and said recess lining section being configured and sized so as to fittingly receive said stabilizing pin; whereby said stabilizing pin is adapted to act as a stabilizing means, in cooperation with said recess peripheral wall for abuttingly limiting the relative range of motion between said prosthesis structure and said base member.

12. An artificial dental structure as recited in claim 11 wherein said stabilizing pin has a conical general configuration, said conical configuration defining an apex, said apex having a generally dome shaped configuration.

13. An artificial dental structure as recited in claim 11 wherein said stabilizing pin has a generally "8"-shaped transversal cross-sectional configuration and a generally "T"-shaped vertical cross-sectional configuration.

14. An artificial dental structure as recited in claim 11 further comprising an anchoring lip that extends integrally and substantially outwardly from said lingual surface of said prosthesis structure adjacent said base surface; said membrane being configured and sized so as to be in an overlapping relationship relatively to said anchoring lip.

15. An artificial dental structure as recited in claim 14 wherein said anchoring lip extends across said lingual surface and said anchoring lip has a slightly curved cross-sectional configuration with said tip of said anchoring lip turning towards said occlusal surface, both said anchoring lip and the membrane section overlapping said anchoring lip being inserted in said base component.

* * * * *